(12) United States Patent
Menendez Gonzalez

(10) Patent No.: US 11,684,746 B2
(45) Date of Patent: Jun. 27, 2023

(54) DEVICE FOR THE SELECTIVE REMOVAL OF MOLECULES FROM TISSUES OR FLUIDS

(71) Applicant: FUNDACION DE NEUROCIENCIAS, Asturias (ES)

(72) Inventor: Manuel Menendez Gonzalez, Asturias (ES)

(73) Assignee: FUNDACION DE NEUROCIENCIAS, Oviedo (ES)

(*) Notice: Subject to any disclaimer, the term of this patent is extended or adjusted under 35 U.S.C. 154(b) by 497 days.

(21) Appl. No.: 16/964,151

(22) PCT Filed: Jan. 28, 2019

(86) PCT No.: PCT/ES2019/070038
§ 371 (c)(1),
(2) Date: Jul. 22, 2020

(87) PCT Pub. No.: WO2019/158791
PCT Pub. Date: Aug. 22, 2019

(65) Prior Publication Data
US 2021/0030941 A1 Feb. 4, 2021

(30) Foreign Application Priority Data
Feb. 14, 2018 (ES) ............................. ES201830130

(51) Int. Cl.
*A61M 25/00* (2006.01)
*A61M 31/00* (2006.01)
(Continued)

(52) U.S. Cl.
CPC ......... *A61M 25/00* (2013.01); *A61B 10/0045* (2013.01); *A61B 10/02* (2013.01);
(Continued)

(58) Field of Classification Search
CPC . A61B 10/0045; A61B 10/02; A61B 10/0283; A61M 1/301; A61M 1/34;
(Continued)

(56) References Cited

U.S. PATENT DOCUMENTS

| 5,209,717 A * | 5/1993 | Schmoll | A61M 1/3615 |
| | | | 604/500 |
| 2008/0091166 A1* | 4/2008 | Fitzgerald | A61B 5/0086 |
| | | | 604/500 |
| 2013/0131614 A1* | 5/2013 | Hassan | A61M 1/84 |
| | | | 604/319 |

FOREIGN PATENT DOCUMENTS

| WO | WO 1988/006045 A2 | 8/1988 |
| WO | WO 2004/083817 A2 | 9/2004 |
| WO | WO 2008/157256 A1 | 12/2008 |

OTHER PUBLICATIONS

International Search Report issued in application No. PCT/ES2019/070038, dated Apr. 4, 2019.

* cited by examiner

*Primary Examiner* — John Kim
(74) *Attorney, Agent, or Firm* — Knobbe, Martens, Olson & Bear, LLP

(57) ABSTRACT

An implantable device is for the selective removal of molecules from tissues or fluids so as to allow the selective removal of a particular molecule of interest (target molecule) from any type of fluid solution or tissue, including biological tissues or fluids. The device operates through the complementary action of specific-binding molecules (antibodies) directed against the target molecule inside the device. The device includes a nanoperforated membrane having pores larger than the target molecule but smaller than (Continued)

the antibodies, such that the fluid can be removed through a second catheter with a lower concentration of target molecules.

4 Claims, 1 Drawing Sheet

(51) Int. Cl.
| | |
|---|---|
| *A61B 10/02* | (2006.01) |
| *A61B 10/00* | (2006.01) |
| *A61M 1/30* | (2006.01) |
| *A61M 1/34* | (2006.01) |
| *A61M 1/36* | (2006.01) |

(52) U.S. Cl.
CPC ......... *A61B 10/0283* (2013.01); *A61M 1/301* (2014.02); *A61M 1/34* (2013.01); *A61M 1/3659* (2014.02); *A61M 1/3679* (2013.01); *A61M 1/3687* (2013.01); *A61M 31/00* (2013.01); *A61M 1/3496* (2013.01); *A61M 2025/0039* (2013.01); *A61M 2210/0693* (2013.01)

(58) Field of Classification Search
CPC .............. A61M 1/3496; A61M 1/3659; A61M 1/3679; A61M 1/3687; A61M 25/00; A61M 31/00; A61M 2025/0039; A61M 2210/0693

See application file for complete search history.

DEVICE FOR THE SELECTIVE REMOVAL OF MOLECULES FROM TISSUES OR FLUIDS

OBJECT OF THE INVENTION

The present invention relates to an implantable device for the selective removal of molecules from tissues or fluids so as to allow the selective removal of a particular molecule of interest (target molecule) from any type of fluid solution or tissue, including biological tissues or fluids.

The device according to the invention also allows the fluid in which the device is positioned to be removed and also allows substances to be administered thereto (for example, to administer enzymes that promote the degradation of deposits of the target molecule).

BACKGROUND OF THE INVENTION

Techniques that involve the removal of macromolecules that are considered mediators of pathological processes from biological fluids have been applied since the beginning of the twentieth century. The most familiar, generally known as plasmapheresis or plasma exchange, comprise separating the cellular component from the liquid in the blood (plasma), which is processed to remove more or less selectively any of its components. After treatment, the plasma is reinfused.

In clinical practice, the terms plasmapheresis and plasma exchange are used synonymously, although in the vast majority of cases the plasma separated from the blood is removed and replaced by the same volume of a replacement solution. However, these techniques suffer from specificity (selectivity), in other words, they remove a large amount of different substances, which may include antibodies, immune complexes, cryoglobulins, complement components, lipoproteins, toxins bound to proteins, and other unknown substances. In fact, the exact mechanism by which plasmapheresis exercises its therapeutic effect is unknown.

Filters/columns for removing endotoxins are extracorporeal devices used to remove endotoxins from the plasma by haemoperfusion/adsorption. They are based on the use of adsorbents made up of resins or charcoal which are capable of removing endogenous and exogenous toxins by combining therewith.

Toraymyxin® incorporates polymyxin B (an antibiotic which is characterised by producing a strong bond with the endotoxin circulating in the blood flow) into polystyrene and polypropylene fibres.

LPS adsorber (Alteco Medical AB) is a device made up of two porous polyethylene discs covered with a synthetic peptide that has a high endotoxin adsorption capacity.

Oxiris (Gambro-Hospal-Baxter) is a polysulphone and polyacrylonitrile filter with the ability to adsorb proinflammatory cytokines and endotoxins (limited clinical trials).

The MATISSE-Fresenius system is based on the affinity of endotoxins with human albumin. This system incorporates albumin in a polymethacrylate filter. Clinical safety and tolerance studies have been carried out. Clinical efficacy yet to be demonstrated.

Cytosorb® is a porous material made of polystyrene and divinylbenzene which reduces circulating cytokine levels (IL-1ra, IL-6, IL-10, IL-8, IL-1) in animal models and in humans with severe sepsis or septic shock. Studies have been carried out on few patients.

A CTR column is a column made up of cellulose combined with a hydrophobic organic ligand. The CTR column makes possible the removal of cytokines and enterotoxins with molecular weights of between 5000 and 50,000 Da. Used in rat studies with satisfactory results.

Removal of Lipoproteins

DALI® is a device that allows the direct adsorption of lipoproteins and LDL cholesterol in patients with hypercholesterolaemia refractory to conventional treatments.

The TheraSorb™ LDL therapy system (Miltenyi Biotec) comprises two reusable adsorption systems (made up of Sepharose), available in different sizes, that remove LDL, Lp (a) and VLDL cholesterol from the patient's blood.

The above-mentioned devices have some selectivity, and undoubtedly more than conventional generic plasmapheresis or extracorporeal filtration techniques. However, they are systems based on the antigen-antibody reaction which introduce a significant element of selectivity (specificity), turning them into formidable tools for the detection, capture and removal of macromolecules with antigenic properties.

A detailed analysis of the advances made so far in the development and validation of systems for the selective removal of molecules based on immunotechnology reveals scant progress. The only immunotechnology-based devices employed at present are used for the removal of pathogenic antibodies and are not based on antigen recognition by the Fab fragment of the antibody and could therefore be classed as semi-selective. Current immunotechnological methods fall within known methodologies such as column immunoadsorption or extracorporeal immunoadsorption.

Extracorporeal immunoadsorption comprises collecting plasma from the patient (using apheresis) and circulating said plasma through a column which selectively removes circulating immune complexes and IgG. The therapeutic removal of antibodies is used in clinical practice to treat a wide range of autoimmune diseases and in organ transplants. They include:

Immunosorba® (Fresenius Medical Care), in which the column contains the highly purified A protein immobilised in a substrate of Sepharose. The immune complexes bind to the protein A and are therefore selectively removed from the plasma. The plasma may be returned to the patient, thus removing the need for a plasma exchange.

GLOBAFFIN® (Fresenius Medical Care) are columns of Sepharose in which the synthetic peptide GAM-146, which has an affinity to antibodies, is immobilised.

Ig-Therasorb® (Miltenyi Biotec, Bergishch-Gladbach), in which, during apheresis treatment, two reusable cartridges selectively remove antibodies and immune complexes from the patient's blood. The columns are covered with sheep anti-human Ig.

Selesorb® (Kaneka Medical Products) is specifically designed for treating systemic lupus erythematosus. SELESORB® is designed to remove anti-DNA antibodies, anti-cardiolipin antibodies and/or immune complexes from patients with SLE. The SELESORB® adsorption mechanism is based on chemisorption by dextran sulphate immobilised on cellulose pearls.

The Asahi Kasei Medical commercial firm in Japan also uses specific filters for neurological diseases (myasthenia gravis, Guillain-Barré syndrome, chronic inflammatory demyelinating polyneuropathy, multiple sclerosis), for autoimmune diseases and for the selective removal of bilirubin and bile acids.

As mentioned above, the therapeutic removal of antibodies in these methods is achieved semi-selectively. A system is under development based on a hollow-fibre specific antibody filter (or extracorporeal-specific antibody filter, SAF) which selectively removes antibodies with a given specificity directly from whole blood, without plasma separation and with minimal removal of plasma proteins other than the directed antibodies. The SAF comprises a hollow-fibre dialysis membrane with specific antigens for directed antibodies immobilised on the inner fibre wall, thus managing to remove only the antibodies of interest, based on the specific antigen-antibody reaction.

All the systems described involve the use of bulky and expensive equipment. Moreover, treatment must be provided as an inpatient. Consequently, filtering systems like those to be developed in the present project are more accessible, more economical, and more selective than those referred to in the prior art.

SUMMARY OF THE INVENTION

The device according to the invention allows the selective removal of molecules of interest in tissues or fluids based on a simple but very effective solution.

More specifically, the device according to the invention is made up of a main catheter, of which the distal end terminates in a chamber with walls that are distinctive in being porous, and having a pore size larger than that of the target molecule, but smaller than that of the antibodies or aptamers provided to bind to said target molecule, thus acting as a semipermeable membrane or nanomembrane.

Thus, the main catheter allows antibodies or aptamers, which are held in the chamber, to be loaded through the surface end of said main catheter.

At the same time, the molecules naturally present in the body fluids or tissues, being smaller, will enter the chamber through the pores, except for those molecules of a size that does not allow this.

Thus, the antibodies will bind to the target molecules inside the chamber such that said target molecules are held inside said chamber.

The process will continue until the capacity of the antibodies is saturated, and may be restarted by aspirating the contents of the chamber through the catheter and infusing a new load of antibodies. Whether the antibodies need to be changed will be determined by measuring the concentration of the target molecule in 9 and in 10. When this difference is small, this will indicate that the antibodies or aptamers are saturated and a reload is required.

Thus, the device operates by the complementary action of specific-binding molecules (antibodies or aptamers) directed against the target molecule inside the device with a nanoperforated membrane that has pores larger than the target molecule but smaller than the antibodies.

Parallel to said catheter and in communication with the main chamber described above is a second catheter, positioned so as to communicate with said chamber through a nanoporous membrane of the same type. The fluid, free from the antibodies administered and having a lower concentration of the target molecule than that present in the tissue, will therefore enter this catheter, as it will in part have been held in the main chamber by the effect of the antibodies.

Finally, the device has a third catheter, totally independent of the previous two, which terminates in a chamber, also independent of the main chamber, and having walls formed of a microporous membrane allowing access thereto by all the molecules in the tissue or fluid, regardless of size. The purpose of this catheter is to remove the fluid in which the device is positioned and/or to allow substances to be administered thereto (for example to administer enzymes that promote the degradation of deposits of the target molecule).

From this structure, the distal end of the device will be implanted in the tissue, vessel or cavity that contains the fluid from which the target molecule is to be removed. The surface end of the three catheters may be positioned at any level accessible from outside. For example, in a living being, said end may be left outside the organism, in which case it would be directly accessible, or under the skin in the subcutaneous cell tissue, in which case each catheter would be covered by a cap accessible from the outside by puncturing.

BRIEF DESCRIPTION OF THE DRAWINGS

To complement the description that follows and to help provide a better understanding of the characteristics of the invention according to a preferred embodiment thereof, a set of accompanying drawings is provided as an integral part of said description for illustrative and non-limiting purposes, showing the following.

DETAILED DESCRIPTION OF THE PREFERRED EMBODIMENT

Figure 1:
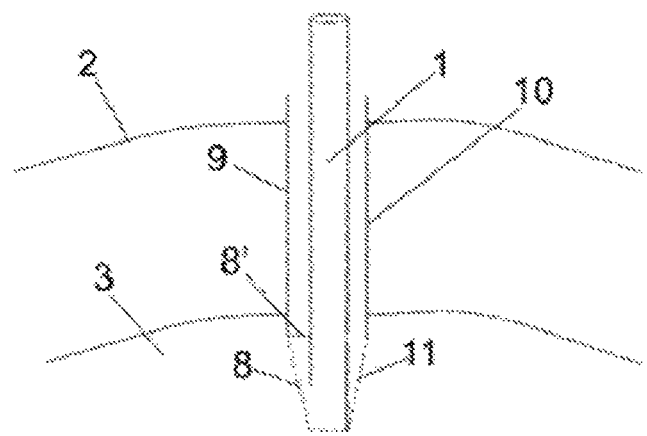
FIG. 1 is a schematic view in profile and in cross section of a device for the selective removal of molecules from tissues or fluids in accordance with the object of the invention.

In the figures provided, it can be seen that the device for the selective removal of molecules from tissues or fluids is made up of a main catheter (1) which is inserted through the body surface (2) in question, until it reaches the fluid (3) or tissue to be treated, in which fluid (3) or tissue a series of target molecules (4) are present, together with natural antibodies (5).

The main catheter (1) ends in a chamber (7) in which a nanomembrane (8) is positioned, having a pore size larger than that of the target molecules (4), but smaller than that of the antibodies, both the natural antibodies (5) present in the fluid or tissue, and the specific antibodies or aptamers (6) which are introduced through the main catheter (1).

Thus, the main catheter (1) allows specific antibodies (6) to be loaded through the surface end thereof, which antibodies are held in the main chamber (7).

At the same time, the target molecules (4) enter the main chamber (7) where they are attacked by the specific antibodies or aptamers (6), which are provided to treat said target molecule.

Thus, a large portion of the target molecules (4) will be held inside the main chamber (7) by the effect of the specific antibodies or aptamers (6), as a second catheter (9) has been provided, positioned parallel to the main catheter and in communication with the main chamber through a nanomembrane (8') having identical characteristics to the nanomembrane (8) described above, through which second catheter the treated fluid is removed, accessing said fluid free from the antibodies administered, and having a lower target molecule concentration than that present in the tissue, as it will in part have been held in the main chamber by the effect of the antibodies.

When the capacity of the antibodies has been saturated, it can be restarted by aspirating the contents of the main chamber (7) through the main catheter (1) and infusing a new load of specific antibodies (6).

Finally, it should be pointed out that the device has a third catheter (10), totally independent of the previous two catheters, which terminates in a secondary chamber (11), also independent of the main chamber (7), having walls formed of a microporous membrane (12), allowing access thereto by all the molecules in the tissue or fluid, regardless of size. The purpose of said third catheter (10) is to allow the fluid in which the device is positioned to be removed and/or to allow substances to be administered thereto (for example to administer enzymes that promote the degradation of deposits of the target molecule).

Figure 2:
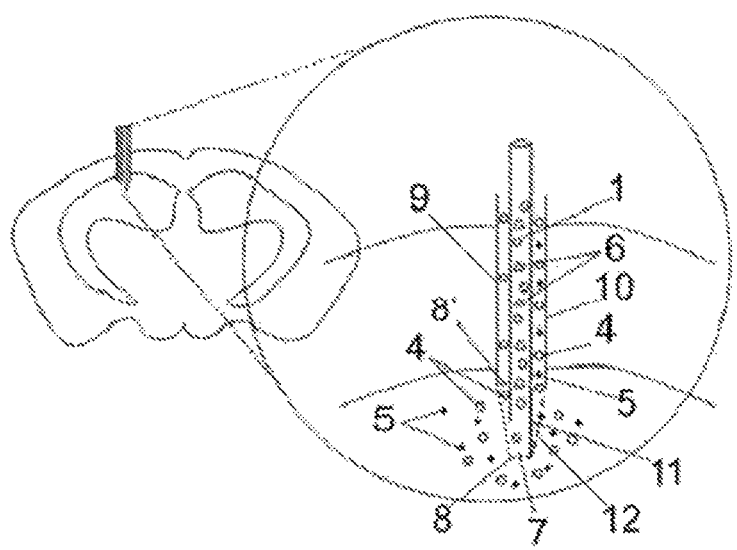
FIG. 2 is a view of the device in the previous figure implanted in the lateral ventricle of the brain of a mouse, showing an enlarged detail in which appear the target molecules, the natural antibodies and the antibodies used to reduce the concentration of target molecules.

From this structure, as can be seen in FIG. 2 in which the device is implanted in the lateral ventricle of a mouse brain, the small molecules in the fluid will enter, free from natural antibodies, freely into the main chamber (7), such that specific antibodies or aptamers (6), in particular monoclonal antibodies specifically directed against the target molecule (4), can be infused, which will bind thereto, preventing the re-entry thereof into the original fluid.

Samples of the fluid (3) may be removed through the third catheter (10), said samples having the actual concentration of target molecules (4) and antibodies (5), while the fluid (3) having a concentration of the target molecule (4) lower than that of the original fluid may be removed through the second catheter (9).

What is claimed is:

1. A device for selective removal of molecules from tissues or fluids, wherein the tissues or fluids comprise target molecules and natural antibodies, wherein said device comprises:
   a main catheter which can be inserted through a body surface, until said main catheter reaches the fluid or the tissue from which selective removal of molecules is desired, the main catheter being configured for inserting specific antibodies or aptamers against the target molecules;
   a main chamber in which the main catheter terminates;
   a first nanomembrane is positioned in the main chamber and having a pore size larger than that of the target molecules, but smaller than that of the antibodies; and
   a second catheter in communication with the main chamber through a second nanomembrane, having a pore size larger than that of the target molecules, but smaller than that of the antibodies, said second catheter thereby providing for removing and filtering fluid treated with the specific antibodies or aptamers and consequently having a lower concentration of target molecules.

2. The device according to claim 1, wherein the device has a third independent catheter, which terminates in a secondary chamber, independent of the main chamber, having walls formed of a microporous membrane which allows access thereto by all the molecules in the tissue or fluid, regardless of size, and allows for the administration of substances to said fluid.

3. A method of selective removal of molecules from tissues or fluids, comprising:
   providing the device according to claim 1;
   inserting the main catheter of the device through the body surface until said main catheter reaches the fluid or the tissue from which selective removal of molecules is desired;
   inserting the specific antibodies or aptamers against the target molecules through the main catheter and into the main chamber in which the first nanomembrane is positioned to produce the fluid treated with the specific antibodies or aptamers;
   passing the fluid treated with the specific antibodies or aptamers through the second nanomembrane into the second catheter; and
   removing and filtering the fluid treated with the specific antibodies and consequently having a lower concentration of target molecules from the second catheter.

4. The method of claim 3, further comprising administering substances to the fluid via a third independent catheter, which terminates in a secondary chamber independent of the main chamber, and having walls formed of a microporous membrane, which allows access by all molecules in the tissue or fluid, regardless of size.

\* \* \* \* \*